United States Patent [19]

Schumacher et al.

[11] Patent Number: 5,053,335
[45] Date of Patent: Oct. 1, 1991

[54] PLASMIDS FOR THE INCREASED PRODUCTION OF PENICILLIN G AMIDASE

[75] Inventors: Günter Schumacher; Peter Buckel, both of Bernried, Fed. Rep. of Germany

[73] Assignee: Boehringer Mannheim GmbH, Mannheim, Fed. Rep. of Germany

[21] Appl. No.: 303,097

[22] Filed: Jan. 27, 1989

Related U.S. Application Data

[63] Continuation of Ser. No. 793,623, Oct. 31, 1985, abandoned.

[30] Foreign Application Priority Data

Oct. 31, 1984 [DE] Fed. Rep. of Germany ....... 3439843

[51] Int. Cl.⁵ .......................... C12N 9/84; C12N 1/21; C12N 15/70
[52] U.S. Cl. ............................... 435/230; 435/252.33; 435/320.1; 935/29; 935/60; 935/73
[58] Field of Search ................. 435/320, 230, 243, 68, 435/27, 60, 172.3, 231

[56] References Cited

U.S. PATENT DOCUMENTS

4,554,250 11/1985 McCullough ..................... 435/172.3

FOREIGN PATENT DOCUMENTS

0107823 5/1984 European Pat. Off. ............ 435/230

OTHER PUBLICATIONS

Burtscher et al., "Folding, Assembly, Stability and Genetic Modification of Penicillin Acylase and Its Precursor", Poster Presented at the "Biotechnology Action Program Final Meeting", Nov. 14–18, 1989, Troia, Portugal.

Böck, A. et al. (1983), FEMS Microbiol. Lett. 20, 135–139, 141–144.

*Primary Examiner*—Elizabeth C. Weimar
*Assistant Examiner*—Charles L. Patterson
*Attorney, Agent, or Firm*—Felfe & Lynch

[57] ABSTRACT

The present invention provides a plasmid suitable for the expression of penicillin G amidase, wherein it carries an incomplete penicillin G amidase gene in which the first 78 bases of the translated region on the 5' end of the complete gene are missing. This incomplete penicillin G amidase gene can also be present incorporated in the form of two separate fragments which commence with bases 79 and 868, respectively, counting from the translated region on the 5' end of the gene and displaying a deletion of the coding bases 705 to 867.

The present invention also provides a process for the production of these plasmids and is also concerned with the use thereof for obtaining penicillin G amidase.

23 Claims, 12 Drawing Sheets

```
         AAGCTTCGTTGCTAGTATCAATTCGCTAATTATACACCTGCCAGAGGATACA

1  MetLysAsnArgGlnArgMetIleValAsnCysValThrAlaSerLeuMetTyrTyrTrp    20
  1  ATGAAAAATAGAAATCCTATGATCGTGAACTGTGTTACTGCTTCCCTGATGTATTATTGG    60
            *         *         *         *         *         *

21  SerLeuProAlaLeuAlaGlyGlnSerSerSerGluIleLysIleValArgAspGluTyr   40
 61  ACCTTACCTGCACTGGCTGAGCAGTCCTCAAGTGAGATAAACATTCTTCGCGATGAATAC   120
            *         *         *         *         *         *

41  GlyMetProHisIleTyrAlaAsnAspThrTrpHisLeuPheTyrGlyTyrGlyTgrVal    60
121  GCCATGCCGCATATTTATGCCAATCATACATGCCACCTATTTTATCGCTATGCCTATGTA   180
            *         *         *         *         *         *

61  ValAlaGlnAspArgLeuPheGlnMetGluMetAlaArgArgSerThrGlnGlyThrVal    80
181  GTAGCACAAGATCGCCTTTTTCAGATGGAAATGGCACGTCCCAGTACTCAACGGACTGTC   240
            *         *         *         *         *         *

81  AlaGlyValLeuGlyLysAspPheValLysPheAspLysAspIleArgArgAsnTyrTrp   100
241  GCGGAAGTGCTTGGCAAAGATTTTGTGAAATTTGATAAAGATATCCGTCGTAACTACTGG   300
            *         *         *         *         *         *

101  ProAspAlaIleArgAlaGlnIleAlaAlaLeuSerProGluAspMetSerIleLeuGln   120
301  CCCGATGCTATCCGGGCGCAAATTGCTGCCCTTTCCCCAGAGGATATGTCCATTCTCCAA   360
            *         *         *         *         *         *

121  GlyTyrAlaAspGlyMetAsnAlaTrpIleAspLysValAsnThrAsnProGluThrLeu   140
361  GCCTACGCTGATGGAATGAATGCCTGGATTGATAAGGTAAATACCAATCCACAGACGCTC   420
            *         *         *         *         *         *

141  LeuProLysGlnPheAsnThrPheGlyPheThrProLysArgTrpGluProPheAspVal   160
421  TTACCAAAACAGTTTAATACATTTGGCTTTACTCCTAAGCGCTGGGAACCGTTTGATGTC   480
            *         *         *         *         *         *

161  AlaMetIlePheValGlyThrMetAlaAsnArgPheSerAspSerThrSerGluIleAsp   180
481  GCCATGATATTTGTGCGCACCATCGCAAACCGCTTCTCTGATAGCACTAGCGAAATTGAT   540
            *         *         *         *         *         *

181  AsnLeuAlaLeuLeuThrAlaLeuLysAspLysTyrGlyValSerGlnGlyMetAlaVal   200
541  AATCTGGCACTCCTAACCCCTTTAAAAGATAAATATCGTGTATCACAAGGCATCGCCCTA   600
            *         *         *         *         *         *
```

FIG.1a.

```
        AAGCTTCGTTGCTAGTATCAATTCGCTAATTATACACCTGCCAGAGGATACA

1 MetLysAsnArQAgnArgMetIleValAsnCysValThrAlaSerLeuMetTyrTyrTrp  20
  1 ATGAAAAATAGAAATCCTATGATCGTGAACTGTGTTACTGCTTCCCTGATGTATTATTGG  60
       *         *         *         *         *         *

21 SerLeuProAlaLeuAlaGlvGlnSerSerSerGluIleLvsTleValArnAspGluTyr  40
 61 ACCTTACCTGCACTGGCTGAGCAGTCCTCAAGTGAGATAAACATTCTTCCGATGAATAC  120
       *         *         *         *         *         *

41 GlyMetProHisIleTyrAlaAsnAspThrTrpHisLeuPheTyrClyTyrGlyTgrVal  60
121 GCCATGCCGCATATTTATGCCAATCATACATGCACCTATTTTATCGCTATGCCTATGTA  180
       *         *         *         *         *         *

61 ValAlaGlnAspArgLeuPheGlnMetGluMetAlaArgArgSerThrGlnGlyThrVal  80
181 GTAGCACAAGATCGCCTTTTTCAGATGGAAATGGCACGTCCCAGTACTCAACGGACTGTC 240
       *         *         *         *         *         *

81 AlaGlvValLeuGlyLysAspPheValLysPheAspLysAspIleArgArgAsnTyrTrp 100
241 GCGGAAGTGCTTGGCAAAGATTTTGTGAAATTTGATAAAGATATCCGTCGTAACTACTGG 300
       *         *         *         *         *         *

101 ProAspAlaIleArqAlaGlnIleAlaAlaLeuSerProGluAspMPtSerIleLeuG]n 120
301 CCCGATGCTATCCGGGCGCAAATTGCTGCCCTTTCCCCAGAGGATATGTCCATTCTCCAA 360
       *         *         *         *         *         *

121 GlyTyrAlaAspGlyMetAsnAlaTrpIleAspLysValAsnThrAsnProGluThrLeu 140
361 GCCTACGCTGATGGAATGAATGCCTGGATTGATAAGGTAAATACCAATCCACAGACGCTC 420
       *         *         *         *         *         *

141 LeuProLysGlnPheAsnThrPheGlyPheThrProLysArgTrpGluProPheAspVal 160
421 TTACCAAAACAGTTTAATACATTTGGCTTTACTCCTAAGCGCTGGGAACCGTTTGATGTC 480
       *         *         *         *         *         *

161 AlaMetIlePheValGlyThrMetAlaAsnArgPheSerAspSerThrSerGluIleAsp 180
481 GCCATGATATTTGTGCGCACCATCGCAAACCGCTTCTCTGATAGCACTAGCGAAATTGAT 540
       *         *         *         *         *         *

181 AsnLeuAlaLeuLeuThrAlaLeuLysAspLysTyrGlyValSerGlnGlyMetAlaVal 200
541 AATCTGGCACTCCTAACCCCTTTAAAAGATAAATATCGTGTATCACAAGGCATCGCCCTA 600
       *         *         *         *         *         *
```

FIG.1b.

```
201 PheAsnGlnLevLysTrpLeuValAsnProSerAlaProThrThrIleAlaValGlnGlu 220
601 TTTAATCAGTTCAAATCeCTCCTAAACCCATCAGCCCCAACCACTATTCCCGTACAAGAC 660
         *         *         *         *         *         *

221 SerAsnTyrProLeuLysPheAsnGlnGlnAsnSerGlnThrAlaAlaLeuLeuProArg 240
661 ACTAACTACCCACTTAAATTTAATCACCAAAACTCCCAAACACCACCTCTCTTCCCACCC 720
         *         *         *         *         *         *

241 TyrAspLeuProAlaProMetLeuAspArgProAlaLysGlyAlaAspGlyAlaLeuLeu 260
721 TACCATTTACCTGCACCAATCCTTCACCCACCACCAAAACGCCCGGATCGCCCACTGCTC 780
         *         *         *         *         *         *

261 AlaLeuThrAlaGlyLysAsnArgGluThrIleValAlaGlnPheAlaGlnGlyGlyAla 280
781 CCCTTAACAGCACCCAACAACCCGGAAACTATTCTTCCACAATTTCCACACCGTCCTCCC 840
         *         *         *         *         *         *

281 AsnGlyLeuAlaGlyTyrProThrThrSerAsnMetTrpValIleGlyLysSerLysAla 300
841 AATCCTCTGGCCCCCTATCCAACGACCAGCAATATCTCCGTTATCCCCAAAACCAAACCC 900
         *         *         *         *         *         *

301 GlnAspAlaLysAlaIleMetValAsnGlyProGlnPheGlyTrpTyrAlaProAlaTyr 320
901 CACCATCCGAAACCAATCATGCTAAATGCTCCCCACTTTCCCTCGTATCCCCCTCCCTAT 960
         *         *         *         *         *         *

321 ThrTyrGlyIleGlyLeuHisGlyAlaGlyTyrAspValThrGlyAsnThrProPheAla 340
961 ACTTATCCTATTCCTCTCCACCGTCCTCeTTATCATCTCACTCCCAATACACCATTTCCC 1020
         *         *         *         *         *         *

341 TyrProGlyLeuValPheGlyHisAsnGlyValIleSerTrpGlySerThrAlaGlyPhe 360
1021 TATCCTCCCCTCCTTTTTCGTCATAATCCTCTCATTTCCTCCCCATCAACCCCACGTTTC 1080
         *         *         *         *         *         *

361 GlyAspAspValAspIlePheAlaGlvArgLeuSerAlaGluLysProGlyTyrTyrLeu 380
1081 CCCCATCATCTCCATATTTTTCCTCAACCCCTCTCCCCACACAAACCACCCTACTACTTC 1140
         *         *         *         *         *         *

381 HisAsnGlyLysTrpValLysMetLeuSerArgCluCluThrIleThrValLysAsnGly 400
1141 CATAATCCTAAGTCCCTGAAAATCTTAACCCCTCACCAAACCATTACCCTCAAAAATCCT 1200
         *         *         *         *         *         *

401 GlnAlaGluThrPheThrValTrpArgThrValHisClyAsnIleLeuClnThrAspGln 420
1201 CAGGCAGAGACCTTTACTGTCTGGCGTACGGTGCATGGCAACATTCTCCAAACTGACCAG 1260
         *         *         *         *         *         *

421 ThrThrClnThrAlaTyrAlaLysSerArgAlaTrpAspGlyLysCluValAlaSerLeu 440
1261 ACCACACAAACCCCTTACCCTAAATCCCCCCCATCCGATGCTAAACAGGTCCCGTCTTTG 1320
         *         *         *         *         *         *
```

FIG.1c.

```
 441 LeuAlaTrpThrHisClnMe-Ly-AlaLysAsnTrpGlnCluTrpThrGlnGlnAlaAla 460
1321 CTGGCCTGGACTCATCACATGAACCCCAAAAATTGCCACCAGTGGACACAGCACCCACCC 1380
        *         *         *         *         *         *

461 LysGlnAlaLeuThrIleAsnTrpTyrTyrAlaAspValAsnGlyAsnIleClyTyrVal 480
1381 AAACAAGCACTCACCATCAACTGGTACTATCCTCATCTAAACCCCAATATTCCTTATCTT 1440
        *         *         *         *         *         *

481 HisThrClyAlaTyrProAspArgClnSerClyHisAspProArgLeuProValProCly 500
1441 CATACTGCTCCTTATCCAGATCCTCAATCACCCCATCATCCCCCATTACCCCTTCCTCCT 1500
        *         *         *         *         *         *

501 ThrGlyLysTrpAspTrpLysClyLeuLeuProPheClvMetAsnProLysValTyrAsn 520
1501 ACCCCAAAATGCCACTCCAAACCCCTATTCCCTTTTGAAATGAACCCTAACCTGTATAAC 1560
        *         *         *         *         *         *

521 ProGlnSerGlyTyrIleAlaAsnTrpAsnAsnSerProGlnLysAspTyrProAlaSer 540
1561 CCCCACTCCCCATATATTCCTAACTCCAACAATTCTCCCCAAAAACATTATCCCCCTTCA 1620
        *         *         *         *         *         *

541 AspLeuPheAlaPheLeuTrpClyClyAlaAspArgValThrCluIleAspArqLeuLeu 560
1621 GATCTCTTTCCCTTTTTCTCCCCTGCTCCAGATCCCGTTACCGACATCCACCGACTCCTT 1680
        *         *         *         *         *         *

561 GluClnLysProArgLeuThrAlaAspGlnAlaTrpAspValIleArgGlnThrSerArg 580
1681 CAGCAAAAGCCACCCT-AACTGCTGATCACGCATCCCATCTTATTCCCCAAACCACTCCT 1740
        *         *         *         *         *         *

581 GlnAspLeuAsnLevArgLeuPheLevProThrLeuClnAlaAlaThrSerGlyLeuThr 600
1741 CACCATCTTAACCTCACCCTTTTTTTACCTACTCTCCAACCAGCCACATCTCCTTTCACA 1800
        *         *         *         *         *         *

601 GlnSerAspProArgArgGlnLeuValCluThrLeuThrArgTrpAspClyIleAsnLeu 620
1801 CAGACCCATCCCCCTCCTCAGTTCCTACAAACATTAACACCTTCCCATCCCATCAATTTG 1860
        *         *         *         *         *         *

621 LeuAsnAspAspGlyLysThrTrpGlnGlnProClySerAlaIleLeuAsnValTrpLeu 640
1861 CTTAATCATCATCCTAAAACCTCCCACCACCCACCCTCTCCCATCCTCAACCTTTCCCTC 1920
        *         *         *         *         *         *

641 ThrSerMetLeuLysArgThrValValAlaAlaValProMetProPheAspLysTrpTyr 660
1921 ACCACTATCTTCAACCCTACCCTACTCCCTCCCCTACCTATCCCATTTCATAACTCCTAC 1980
        *         *         *         *         *         *

661 SerAlaSerElyThrGluThrThrGlnAspGlyProThrGlySerLeuAsnIleSerVal 680
1981 AGCGCCAGTCCCTACGAAACAACCCAGGACGGCCCAACTCGTTCCCTCAATATAACTCTT 2040
        *         *         *         *         *         *

681 GlyAlaLysIleLeuTyrCluAlaValGlnClyAspLysSerProIleProClnAlaVal 700
2041 GGAGCAAAAATTTTCTATCAGGCGGTCCAGGGAGACAAATCACCAATCCCACAGGCGGTT 2100
        *         *         *         *         *         *
```

FIG.1d.

```
701  AspLeuPheAlaClyLysProGlnGlnCluValValLeuAlaAlaLeuCluAspThrTrp 720
2101 GATCTGTTTCCTGCGAAACCACAGCAGGAGGTTGTGTTCCCTCCCCTGCAACATACCTCC 2160
         *         *         *         *         *         *

721  GluThrLeuSerLysArgTyrGlyAsnAsnValSerAsnTrpLysThrProAlaMetAla 740
2160 CACACTCTTTCCAAACGCTATGGCAATAATGTGAGTAACTGGAAAACACCTGCAATGGCC 2220
         *         *         *         *         *         *

741  LeuThrPheArgAlaAsnAsnPhePheGlvValProClnAlaAlaAlaGluGluThrArq 760
2221 TTAACCTTCCGGGCAAATAATTTCTTTCGTGTACCGCAGGCCGCAGCCGAACAAACCCCT 2280
         *         *         *         *         *         *

761  HisGlnAlaGl~TyrGlnAsnArgGlyThrGluAsnAspMetIleValPheSerProThr 780
2281 CATCACCCGGACTATCAAAACCGTGGAACAGAAAACGATATGATTGTTTTCTCACCAACG 2340
         *         *         *         *         *         *

781  ThrSerAspArgProValLeuAlaTrpAspValValAlaProGlyGlnSerGlyPheTle 800
2341 ACAAGCCATCGTCCTGTGCTTGCCTGEGATGTGGTCCCACCCGGTCAGAGTCGGTTTATT 2400
         *         *         *         *         *         *

801  AlaProAspClyThrValAspLysHisTyrGluAspClnLeuLysMetTyrGluAsnPhe 820
2401 GCTCCCGATGGAACAGTTGATAAGCACTATGAAGATCAGCTGAAAATGTACGAAAATTTT 2460
         *         *         *         *         *         *

821  GlvArgLysSerLeuTrpLeuThrLysGlnAspValGluAl~HisLysGluSerGlnClu 840
2461 CCCCCTAAETCGCTCTGCTTAACGAAGCAGGATGTGCAGGCGCATAACGAGTCCCACGAA 2520
         *         *         *         *         *         *

841  ValLeuHisValClnArg *                                          860
2521 GTGTTGCACGTTCAGACATAA                                         2580
         *         *         *         *         *         *
```

PLASMIDS FOR THE INCREASED PRODUCTION OF PENICILLIN G AMIDASE

This application is a continuation, of application Ser. No. 793,623, filed Oct. 31, 1985, now abandoned.

The present invention is concerned with a plasmid which is suitable for the expression of penicillin G amidase, micro-organisms containing this plasmid and a process for its production, as well as with the use thereof for the production of penicillin G amidase.

Penicillin G amidase, which is also called penicillin acylase (penicillin G amidohydrolase, E.C. 3.5.1.11), catalyses the splitting of penicillin G into 6-aminopenicillanic acid and phenylacetic acid. 6-Aminopenicillanic acid is the precursor for a large number of industrially produced semi-synthetic antibiotics. Therefore, there is a need for large amounts of this enzyme.

One possiblity for achieving this is to clone the penicillin G amidase-coding gene into a plasmid which is present in the cells in a high copying number (about 50). However, in comparison with the induced original strain ATCC 11105, there is hereby only observed an increase by a factor of 5 (see H. Mayer, J. Collins and F. Wagner (1979) in Plasmids of Medical, Environmental and Commercial Importance (ed. K. N. Timmis and A. Pühler) pp. 459–469; pub. Elsevier/North-Holland Biomedical Press, Amsterdam). Attempts to induce the penicillin G amidase-coding gene to a high synthesis capacity in an appropriate expression vector showed that this results in the lysis of the host cells. This shows that by increased expression of the wild type alleles of the penicillin G amidase-coding gene, the desired object of a high synthesis capacity is not achieved.

The information for an enzyme is contained in the desoxyribonucleic acid (DNA). This DNA is converted by a DNA-dependent RNA polymerase into mRNA (ribonucleic acid messenger). The so synthesised mRNA in converted on the ribosomes into protein, in each case 3 nucleotides (triplet or codon) thereby determining, according to the laws of the genetic code, the incorporation of a particular amino acid.

Control regions on the DNA plane determine at which point a strand of the DNA is converted into mRNA (promotor sequences) or at which point the synthesis of the mRNA is stopped (termination sequences).

Stop and start sequences are also known on the plane of the protein synthesis (translation). In general, an ATG (which is converted into f-methionine) thereby determines the beginning of a protein and, for example, a TAA or a TAG the end of the translation.

Knowledge of gene expression is described, for example, in B. Lewin, Gene Expression, Vol. 1, 1974, pub. John Wiley & Sons Ltd.).

The new combination of DNA fragments takes place, as is known, in such a manner that first the DNA is cut with nucleases which "recognise" particular DNA sequences at points containing these sequences. Since a large number of restriction endonucleases is known each of which cut particular DNA points, DNA sequences can, as desired, be cut in a quite definite manner by choice of appropriate nucleases. Such restriction endonucleases make either blunt or protruding ends in the double-stranded DNA. The linking of blunt or protruding ends takes place by enzymes called ligases, usually with the help of the enzyme $T_4$ DNA ligase.

It is an object of the present invention to solve the problem of making the enzyme penicillin G amidase available in large amounts.

In particular, it is an object of the present invention to provide an expression vector of penicillin G amidohydrolase which results in a high synthesis capacity without leading to the lysis of the host cells.

Thus, according to the present invention, there is provided a plasmid suitable for the expression of penicillin G amidase, wherein it carries an incomplete penicillin G amidase gene in which the first 78 bases of the translation region on the 5' end of the complete gene are missing.

A plasmid is an extrachromosomal DNA molecule. This molecule carries the information for multiplying itself (replication origin) and, in addition, one or more selectionable properties, for example a resistance to an antibiotic. These properties permit the preferred recognition of those host cells which carry the desired plasmid. Furthermore, these plasmids have the property that they can be split with one or other restriction enzyme at definite points. Subsequently, after insertion of other DNA fragments, for example split with restriction enzymes, with linking of the ends, a new plasmid can be obtained. A number of plasmids which are especially suitable for such manipulations are already commercially available, for example plasmid pBR 322.

Methods of recombinant DNA technology: DNA splitting and putting together of appropriate DNA fragments to give the new plasmid according to the present invention takes place in vitro outside of the cell. The resulting new expression plasmid can be transferred into a new host cell (micro-organism) by a process which is known as transformation. With the proviso that the DNA segment which codes the desired gene product is present under the control of appropriate transcription and translation starts, the polypeptide sequence of the enzyme can be expressed by this micro-organism. If necessary, after lysis of the host cells and further purification steps, the gene product can be obtained separated from other proteins.

The present invention is based upon the surprising knowledge that the natural penicillin G amidas gene consists of a gene section which codes a polypeptide of 846 amino acids and consists of a preceding promotor sequence, whereby a peptide of 54 amino acids, which occupy positions 236 to 289, is apparently responsible for the insufficient synthesis capacity of the complete gene in the case of expression by a micro-organism after previous incorporation into a plasmid. Therefore, if the coding bases 705 to 867 of the gene responsible for this are removed, the expression inhibition is removed.

There are thus obtained two gene sections which code two shortened polypeptides beginning with methionine. These shorter polypeptides, when they are expressed together, are biologically active with one another and appear to correspond to the naturally occurring enzyme which consists of two subunits. Therefore, the plasmid according to the present invention can also contain the incomplete penicillin G amidase gene in the form of two separate fragments which are represented by these two gene sections, whereby these fragments begin with the bases No. 79 and No. 868, respectively, and a deletion of the coding bases from 705 to 867 is present, counted from the 5' end of the complete gene. Since the complete gene contains 2568 bases, in the following that gene section which begins with base 79 and ends with base 705 and which codes a subunit of the biologically active enzyme obtained according to the present invention is called the small subunit (alpha) and the gene section beginning with base 868 and ending with base 2541 (including stop codon) or 2538 (only translating region) which codes the second subunit of the biologically active enzyme obtainable according to the present invention is called the large subunit ($\beta$).

It is assumed that in the case of the natural enzyme, in the scope of the so-called protein maturation, the biologically active enzyme is first formed with splitting of the primarily produced protein and formation of two subunits which occur together as the active enzyme. Since the protein maturation represents a limiting occurrence for the enzyme expression, by arrangement of the two separate gene sections for the alpha and $\beta$-subunits, a further increase of the expression of biologically active enzyme can be achieved according to the present invention. In front of each gene section, there is then newly introduced a start codon, usually in the form of the codon ATG. Besides this codon, on the 5' end of each "incomplete" gene according to the present invention there must also be introduced promotor sequences which make possible the translation into mRNA, preferably the lac promotor or the tac promotor. However, other promotors can also be used.

For the better recognition of the micro-organisms which contain this plasmid, the plasmid according to the present invention preferably contains at least one resistance gene against chloramphenicol, tetracycline and/or kanamycin. Therefore, in a medium which contains an antibiotic corresponding to the particular resistant gene present, only those micro-organisms grow which contain the plasmid according to the present invention. However, such a resistance gene is in itself not necessary for the present invention.

The present invention also provides micro-organisms which are characterised by a content of at least one plasmid according to the present invention. If the plasmid according to the present invention only contains the gene fragment for the large or for the small subunit, then, for the formation of the biologically active enzyme according to the present invention, it is necessary either that the micro-organism contains not only a plasmid with the gene fragment for the small subunit but also a plasmid with the gene fragment for the $\beta$ subunit or contains a plasmid which codes both subunits. However, if desired, it is also possible that one micro-organism contains only one plasmid for one of the two subunits. In this case, the culturing of the micro-organism takes place in a mixture with a further micro-organism which contains the plasmid for the other subunit. In the latter case, it is preferable to use the same host micro-organisms for both plasmids. Alternatively, the culturing of the two micro-organisms, each of which forms one enzyme subunit, can take place separately. The extracts are then first mixed, with the formation of the active enzyme. As host organisms, there can be used those generally employed in gene technology, preferably derivatives of the *Escherichia coli* K12 strain. Especially good results have been achieved with the *Escherichia coli* strains 54-2 $\Delta$ (lac, pro) rec A, rpsl, F'lac iq, DSM 3066 and DS 410, min A, min B, rpsl, sup+, DSM 3065 and DSM 3058.

In a preferred embodiment, an *Escherichia coli* strain 3058 carries the plasmid pBT 212 according to the present invention. With this, after digestion of the cells and after incubation of the cell extract for 4 to 8 hours, there can be obtained the active penicillin G amidase consisting of the $\alpha$- and $\beta$-subunits.

For the production of the plasmids according to the present invention, it is preferable to use known and largely commercially available starting plasmids which are especially suitable for expression into certain micro-organisms. For example, the plasmid pBR 322, which is commercially available, is especially suitable for expression into all *Escherichia coli* strains and is, therefore, also preferably used within the scope of the present invention. Therefore, the following description of the production of the plasmids according to the present invention starts from derivatives of the plasmid pBR 322 which, in turn, are either commercially available or can be produced from this plasmid in known manner. However, for host organisms other than *Escherichia coli*, other base plasmids are better suited and, therefore, if there is used a host organism which does not belong to the *Escherichia coli*, then it is preferable to start from a plasmid which can be especially well expressed into this host organism. Such plasmids are well known and do not need to be described here in detail. They are described, for example, in the ATCC Catalogue of Strains I.

The production of the plasmids according to the present invention takes place according to known methods, using suitable naturally occurring restriction splitting sites or ones produced synthetically in order to bring the incomplete penicillin G amidase gene under the control of a functionally efficient promotor. Examples of suitable promotors include the tac promotor (see F. Amann, J. Brosius and M. Ptashne, Gene, 1983) and the lac promotor (see L. Guarente et al., Cell, 20, 543-553/1980).

The present invention is described in more detail in the following, with reference to the accompanying drawings, in which:

FIG. 1 (a–d) shows the nucleotide and protein sequence of the complete penicillin G amidohydrolase gene;

The production of DNA preparations, cutting of DNA with restriction endonucleases, putting together of DNA fragments and the conditions for the transformation of host organisms described in the following are per se known and are described, for example, in Advanced Bacterial Genetics (1980), Cold Spring Harbor Laboratory, by R. W. Davis, D. Botstein and J. R.

Roth, as well as in Molecular Cloning (1982), Cold Spring Harbor Laboratory, by T. Maniatis, E. F. Fritsch and J. Sambrook.

Figure 1D:
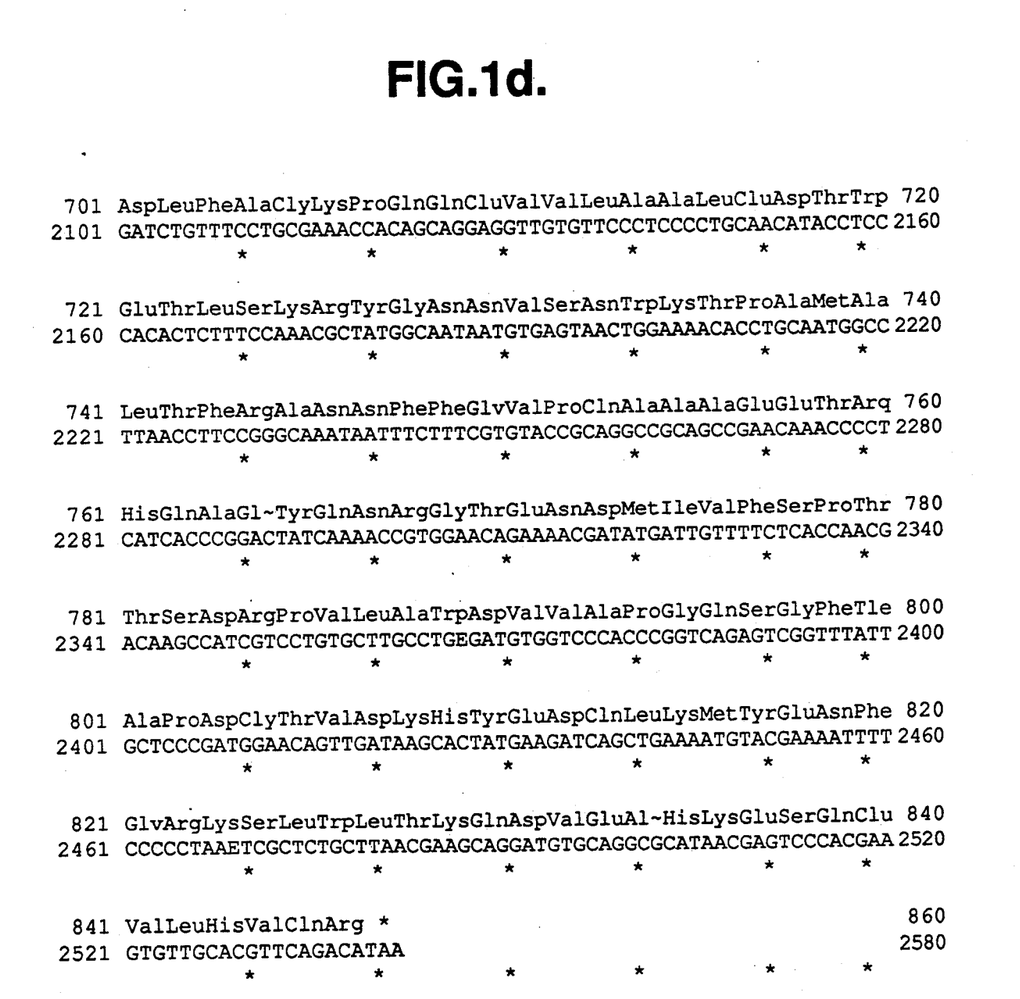

FIG. 1 shows the complete penicillin G amidase gene of 2538 translated nucleotides in the orientation of 5' to 3', i.e. corresponding to the coding mRNA. In each case, 3 (triplet) of the 4 possible nucleotides A, G, C and T determine an amino acid (upper row). The incomplete penicillin G amidase gene contained in the plasmid according to the present invention begins with the triplet GAG in positions 79 to 81, which codes Glu. The fragment coding the small subunit also begins at this point. The fragment coding the large subunit of the enzyme begins in position 868 with the triplet AGC which codes the amino acid Ser and ends at position 2538 with the triplet AGA for Arg. This is followed by the stop codon TAA which can be present in the plasmid according to the present invention but does not have to be. The gene fragment coding the small subunit ends with the amino acid Ala with the triplet GCA in position 703–705.

The plasmids produced according to the present invention take into account for the construction on the DNA plane exactly the carboxy and amino termini of the matured subunits present because of the protein sequence. However, it is known that, in many cases, the addition or removal of amino acids on the carboxy and on the amino terminus does not influence the enzyme activity. Thus, for example, the fusion protein illustrated in FIG. 3 and produced from penicillin G amidase and β-galactosidase, on the amino terminus also about 120 amino acids of the penicillin G amidase. This fusion protein shows the enzyme activity of β-galactosidase. Therefore, the present invention also includes such alterations insofar as the enzyme activity is thereby retained.

Figure 2:
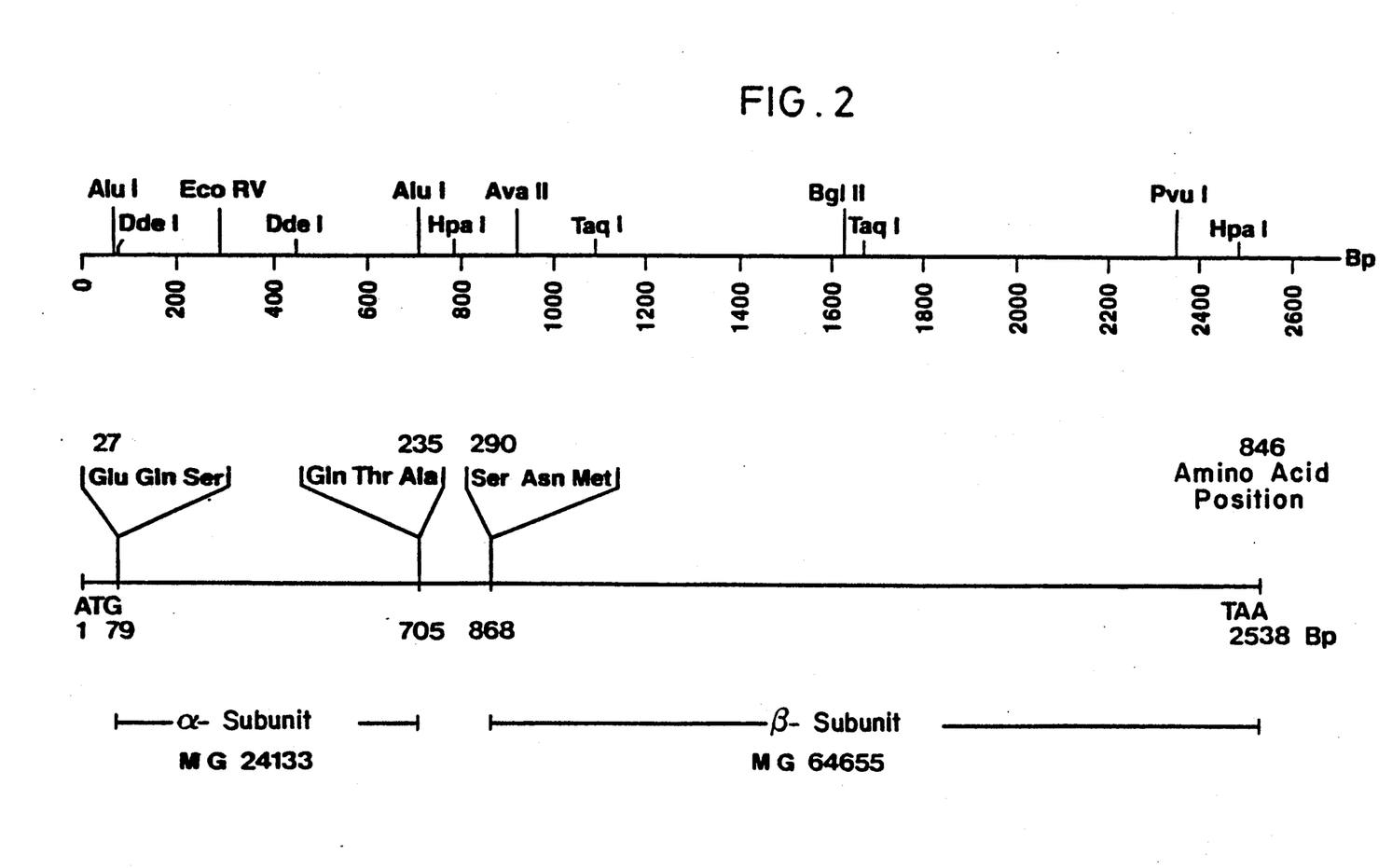
FIG. 2 shows in the upper part a schematic illustration of the restriction endonuclease cutting points relevant for the cloning and, in the lower part, the relevant amino acid sequences of the amino and carboxy termini of the small and of the large subunits of the matured penicillin amidohydrolase.

FIG. 2 explains this in more detail and in the lower part shows schematically, in each case, the beginning of the small and of the large subunit, the molecular weight thereof and the end. The upper part shows the points of fission for a series of nucleases which are utilised in the case of the construction described in the Examples.

From the above, it follows that a plasmid in accordance with this invention contains one of the two fragments depicted in FIG. 1, that is either the fragment beginning with base 79 and ending with base 705, or the fragment beginning with base 705 and ending with base 2538, or the plasmid contains both fragments, either joined together or separated from one another. According to the present invention, these plasmids are used for the production of penicillin G amidase in that a microorganism which contains the plasmid or plasmids according to the present invention is cultured with the expression of the enzyme and the enzyme is recovered from the micro-organism and/or from the culture broth. As micro-organism, it is hereby preferred to use *Escherichia coli* K12 54-2 or DS 410. The latter strain is characterised by an especially good stability against lysis due to overproduction of the periplasmatic enzyme penicillin G amidase.

The following Examples are given for the further explanation of the present invention:

EXAMPLE 1

Figure 3:
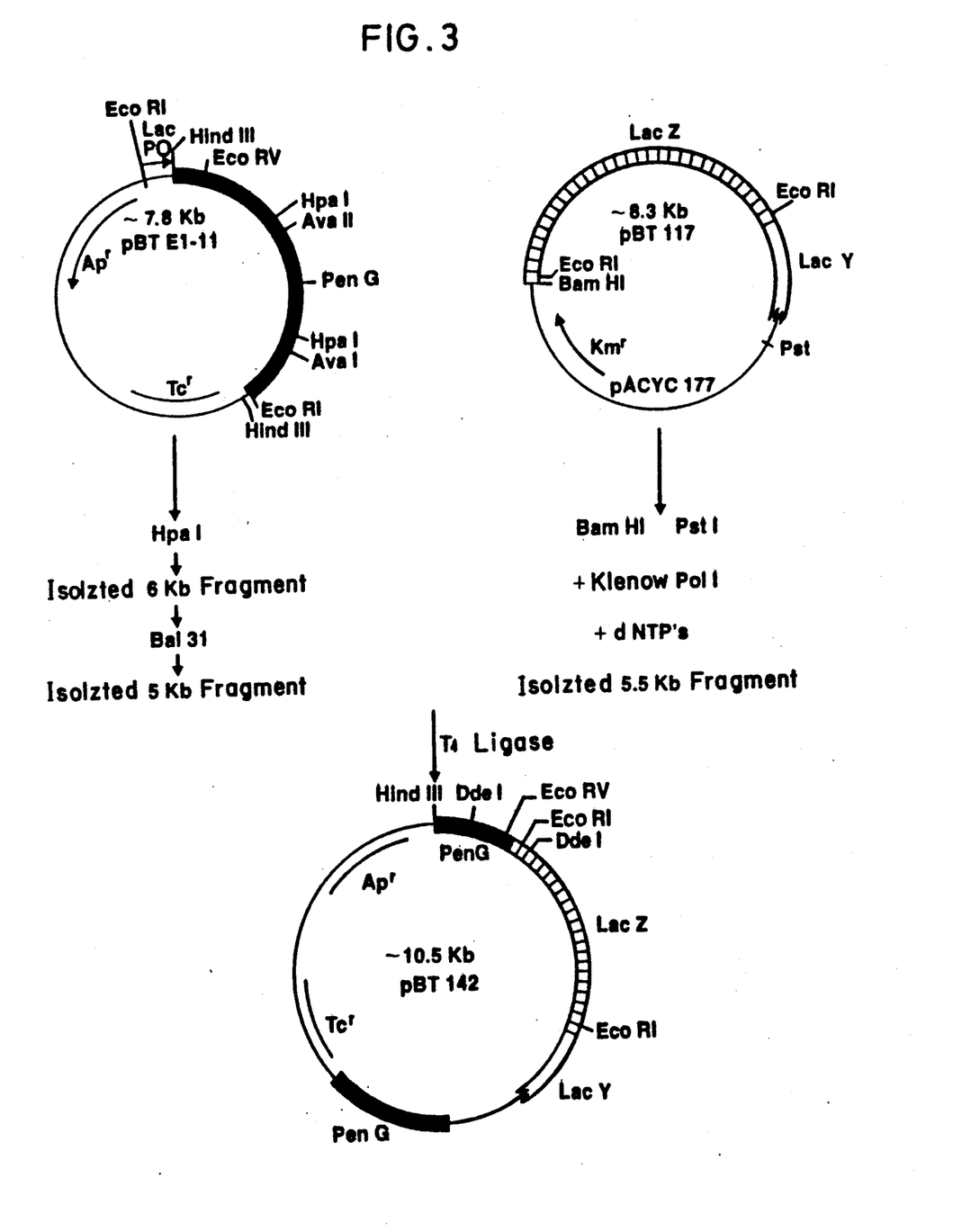
FIG. 3 shows schematically the construction of a fusion protein which is coded by sequences of penicillin G amidase and $\beta$-galactosidase.
Figure 9:
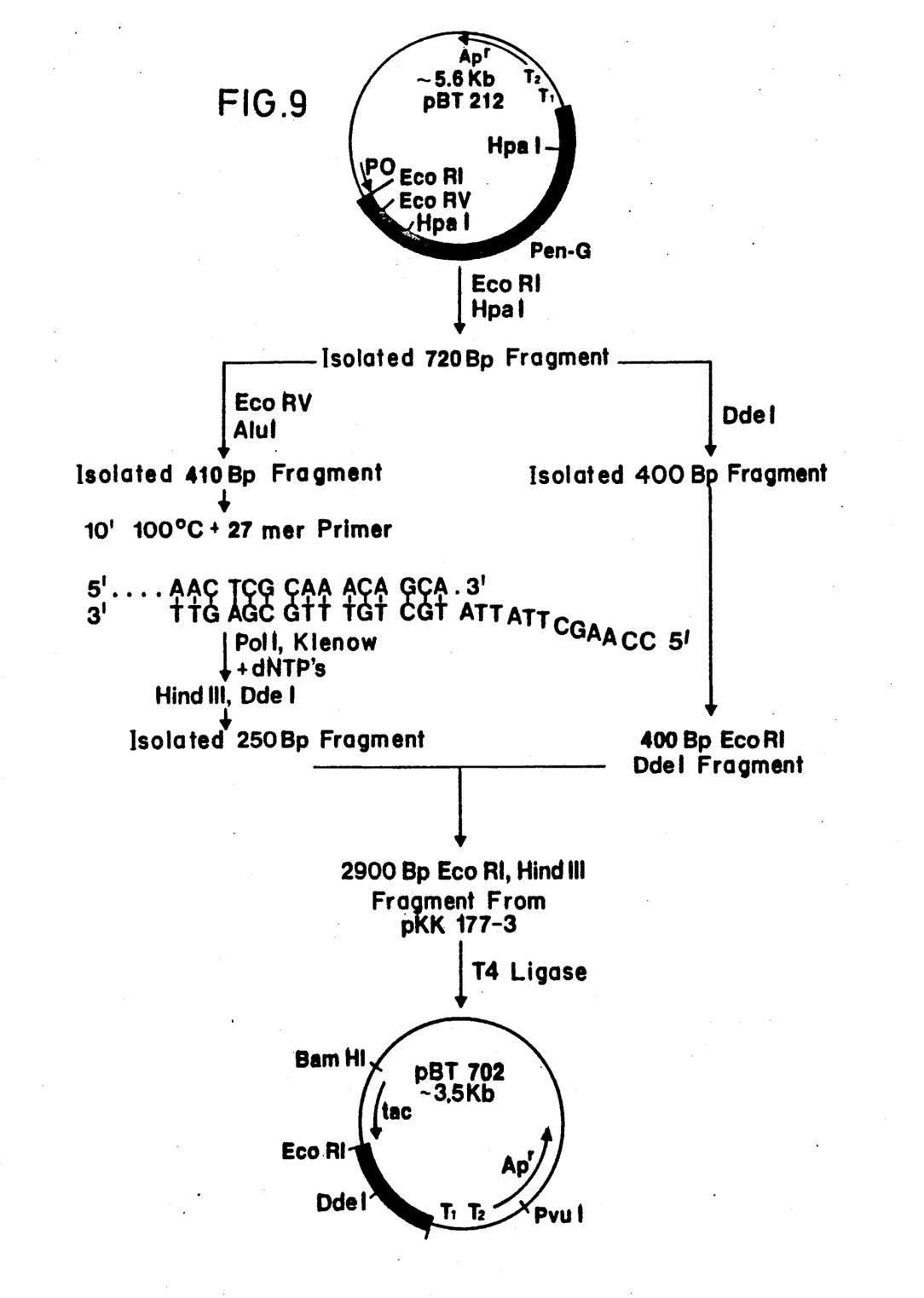
FIG. 9 shows the construction of plasmid pBT 702, DSM 3067P according to the present invention which codes the small subunit of penicillin G amidase and can bring about its expression.

Production of plasmid pBT 212 (FIGS. 3 to 6 of the accompanying drawings) and pBT 702 (FIG. 9 of the accompanying drawings)

pBT E1-11, DSM 3061, is used as the starting plasmid. This plasmid contains an approximately 3 Kb-sized penicillin G amidase coding gene which is schematically illustrated in FIG. 3 as a thick black line. The base sequence of this gene is illustrated in FIG. 1. It codes the enzymatically active polypeptide of 846 amino acids which is also illustrated in FIG. 1. In the case of the natural complete gene, this polypeptide is split three times posttranslationally. The peptide hereby split off from positions 1 to 26 has the size and the properties of a leader peptide (also called a signal peptide). For the construction according to the present invention of this penicillin G amidase without this leader peptide, plasmid pBT 142, DSM 3059 is used as starting material. This plasmid codes a protein which consists aminoterminally of about 120 amino acids of the penicillin G amidase and on which there is distally fused β-galactosidase, beginning with the fifth amino acid.

Plasmid pBT E1-11 (FIG. 3) is split with restriction endonuclease Hpa I and a 6 Kb-sized fragment isolated after size separation in a low melting agarose gel. About 500 base pairs (bp) are removed from each end of this DNA fragment with endonuclease Bal 31.

Plasmid pBT 117, DSM 3063 (FIG. 3) contains the β-galactosidase gene with regulation sequences, i.e. without promotor and operator and with start signal (ATG). From plasmid pBT 117, after splitting with Bam HI and Pst I and making up or splitting off of the protruding ends by means of DNA polymerase I (Klenow fragment) in the presence of 4 desoxyribonucleotide triphosphates (dATP, dTTP, dCTP and dGTP), there is isolated a 5.5Kb-sized fragment (FIG. 3) by size fractionation in a low melting agarose gel. 1 μg. of this fragment is incubated overnight with 0.2 μg. of the 5 KB-sized fragment from pBT E1-11 with 10 units of T4 ligase. The ligation batch is transformed into the strain *Escherichia coli* K12 54-2. Selection takes place on indicator plates which contain X-Gal (see J. H. Miller (1972) in Experiments in Molecular Genetics, Cold Spring Harbor Laboratory, 47–55) and ampicillin. Plasmids of β-galactosidase-positive clones were characterised by splitting with Eco RI, one of these plasmids being pBT 142 (FIG. 3).

Figure 4:
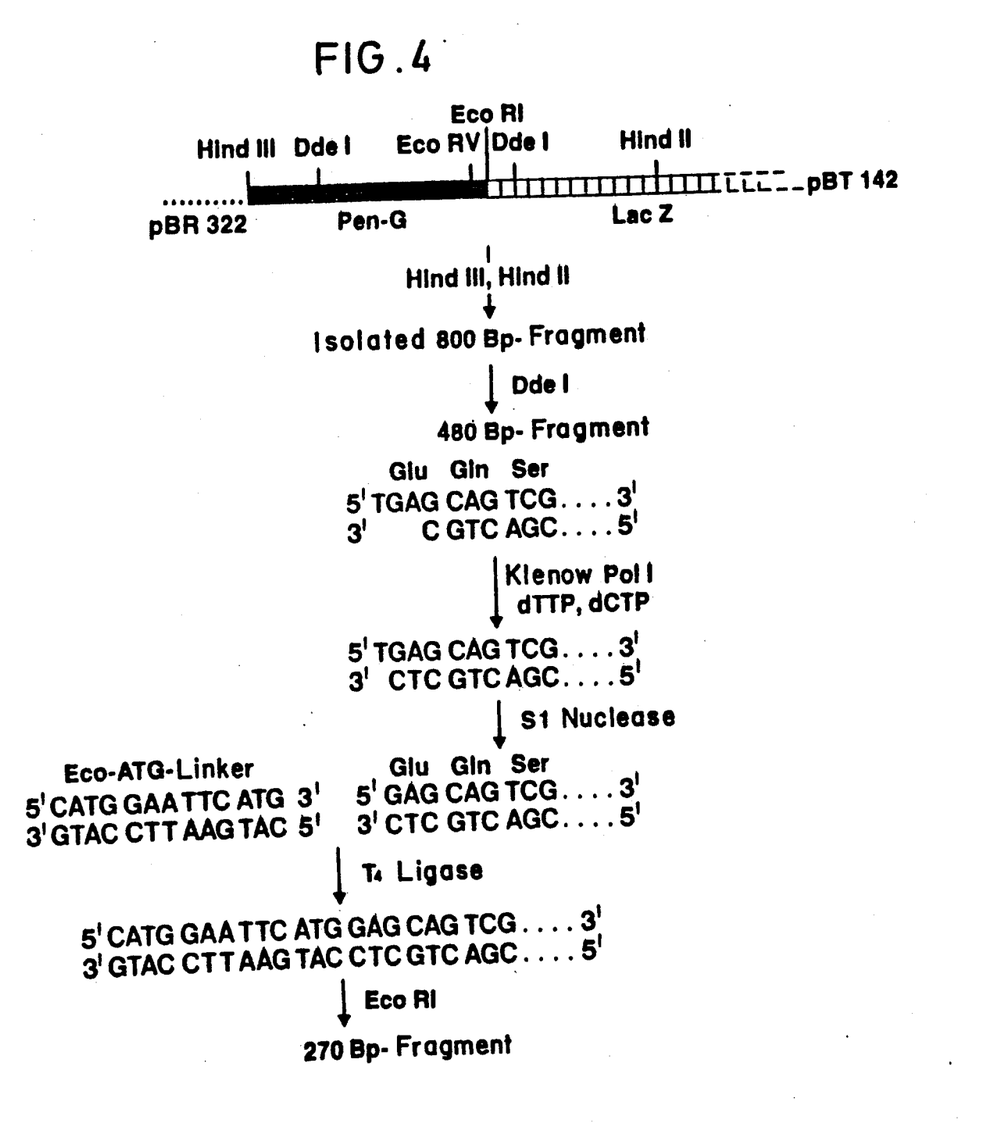
FIGS. 4 to 6 show the construction of the plasmid pBT 212, which is suitable for the expression of a protein, which contains the sequence of penicillin G amidase and can be matured to the active enzyme.

40 μg. of plasmid pBT 142 are split completely with Hind III and Hind II and, after size fractionation, a 800 Bp fragment is isolated. This fragment is split with Dde I and a 480-sized fragment thus obtained.(FIG. 4). After purification of this fragment by size fractionation in a low melting agarose gel, the remaining ends are filled with DNA polymerase I (Klenow fragment) and the desoxyribonucleotide triphosphates dTTP and dCTP by 2 nucleotides. 0.1 μg. of the fragment is incubated for 30 minutes at 30° C. with 1 Unit of S1 nuclease in a buffer which contains 200 mmol/liter of sodium chloride, 50 mmol/liter of sodium acetate (pH 4.5), 1 mmol/liter of zinc sulphate and 0.5% of glycerol. The ribonucleotide dTMP protruding on the 5' end is hereby split off.

The resulting DNA fragment contains a blunt end and the first triplet (GAG) codes the first amino acid (Glu) of the matured form of the small subunit of the penicillin G amidase. In order to ensure a start of the protein synthesis, an ATG is added before the triplet GAG.

By means of the phosphotriester method (see R. Crea, A. Kaszewski, T. Hiros and K. Itakura, Proc. Natl. Acad. Sci. USA, 75, 5765–5769/1978), there is synthesised an EcoATG linker with the base sequence:

5'CATGGAATTCATG3'

3'GTACCTTAAGTAC5'.

This linker is phosphorylated with polynucleotide kinase and a 100 fold excess of this director is ligated with the help of T₄ ligase on the blunt end of the Dde I fragment as previously described. Subsequently, it is completely split with 100 Units of Eco RI and a 0.27 Kb fragment isolated by means of an agarose gel.

Plasmid pKK177-3, DSM 3062 is completely split with Eco RI and Pst I. A 2.9 Kb-sized fragment is isolated by means of size fractionation in agarose gel. pBT 117 is limited with F completely split with Pst I. A 5.5 Kb sized fragment is isolated therefrom (FIG. 5) by size fractionation in agarose gel.

Figure 5:
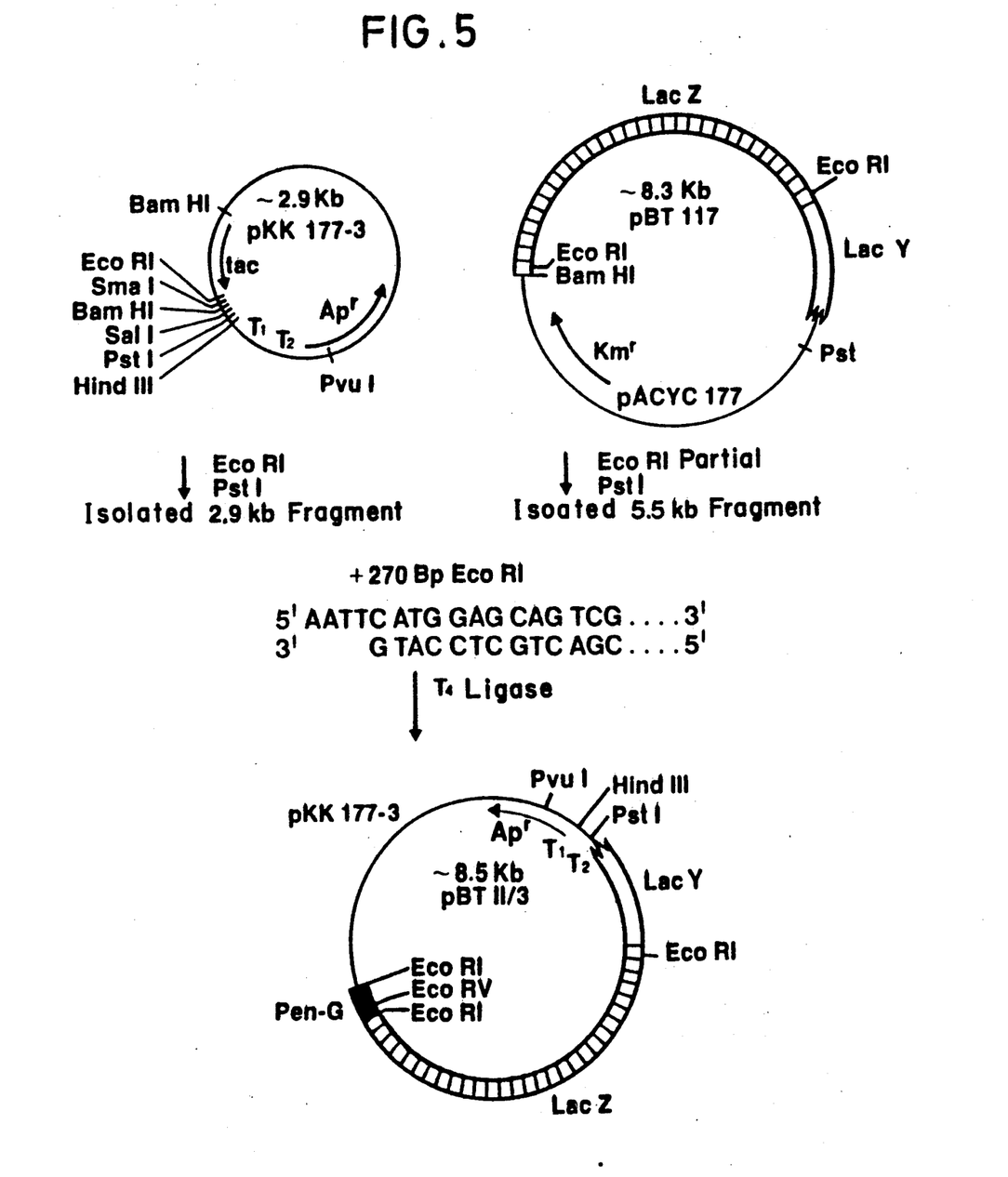
Figure 6:
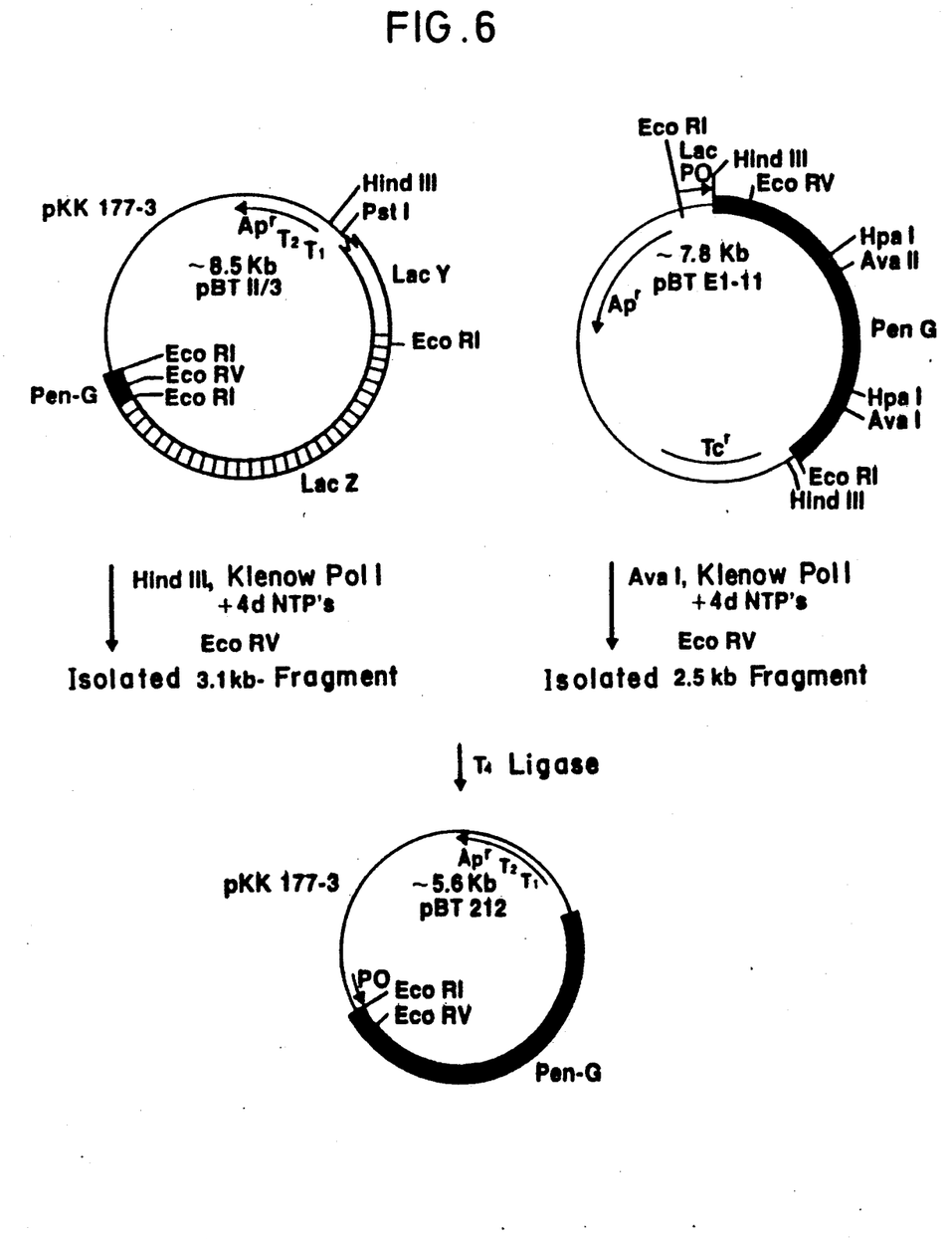

About 100 ng. of the 2.9 Kb vector fragment from pKK 177-3 are ligated with 200 ng. of the 5.5 Kb lac Z fragment from pBT 117 and 100 ng. of the 270 Bp-sized Eco RI fragment overnight with 10 Units of T₄ ligase. After the transformation of Escherichia coli 54-2, β-galactosidase-positive clones are identified on X-gal indicator plates (see J. H. Miller (1972) in Experiments in Molecular Genetics, Cold Spring Harbor Laboratory, 47–55). By means of Eco RI splitting of the plasmid DNA and sequence analysis, there is confirmed the desired construction in the plasmid pBT II/3, DSM 3060 (FIG. 5). Via the Eco RV restriction site the β-galactosidase-coding DNA can be removed and the penicillin G amidohydrolase-coding region restored (FIG. 6). Plasmid pBT II/3 is completely split with Hind III, the protruding ends are filled with polymerase I (Klenow fragment) and 4 desoxyribonucleotide triphosphates, completely split with Eco RV and subsequently a 3.1 Kb fragment isolated after size fractionation. From pBT El-11, there is isolated a 2.5 Kb fragment via Eco RV and Ava I splitting. Before the Eco RV splitting, the protruding Ava I ends are made blunt with polymerase I (Klenow fragment) and all 4 desoxyribonucleotide triphosphates. Both fragments (3.1 Kb and 2.5 Kb) are ligated in the same amount ratios with T₄ ligase. The resulting plasmid is pBT 212, DSM 3058. This plasmid codes a penicillin G amidase without signal sequence (FIG. 6).

From plasmid pBT 212, there is isolated, by splitting with Eco RI and Hpa I, and approximately 720 Bp fragment and from this fragment, after splitting with Eco RI and Dde I, there is isolated an approximately 400 Bp fragment and, after splitting with Alu I and Eco RV, a 410 Bp fragment.

On to the Eco RV, Alu I fragment, after denaturing of the double strand, there is hybridised a 27 primer with the sequence:

5' CCA AGC TTA TTA TGC TGT TTG CGA GTT 3'.

This primer, synthesised according to the phosphotriester method (see Crea et al., Proc. Natl. Acad. Sci. USA, 75, 5765–5769/1978), is homologous to the non coding strand from position 691 to 705 and contains the stop codon TAA twice and a Hind III recognition sequence.

With DNA polymerase (Klenow fragment) and the desoxytriphosphates necessary for the DNA synthesis, the nonhybridising 3' end is split off exonucleolytically and the strand made up from 5' in the direction of 3'. The DNA is split with Hind III and Dde I and an approximately 250 Bp fragment isolated. The vector molecule pKKl 77-3 split with Eco RI and Hind III, the approximately 0.4 Kb Eco RI, Dde I fragment and the approximately 0.25 Kb Dde I, Hind III fragment are linked with the help of the enzyme T₄ ligase (see FIG. 9).

The plasmid so formed codes the small subunit (alpha) of penicillin G amidohydrolase and has the designation pBT 702, DSM 3067P.

EXAMPLE 2

The Escherichia coli strain DSM 3058 carrying the plasmid pBT 212 is cultured overnight at 37° C. in complete medium in the presence of the inductor isopropyl thiogalactoside (IPTG). The cells are collected, digested and the cell extract incubated at 30° C. for 4 to 8 hours. Analysis of the product resulting by the post-incubation at 30° C. in SDS-acrylamide gel shows that a maturing of the precursor proteins into the α- and β-subunits of the penicillin G amidase has taken place. With the appearance of the two subunits, the enzyme activity can be measured, i.e. proteolytic splitting and correct combination to the active enzyme takes place in the cell extract.

Therefore, by enrichment of the specific protease, a quantitative splitting of the precursor protein to the active enzyme is possible.

EXAMPLE 3

Construction of a plasmid for the expression of the large subunit (β) of penicillin G amidase For the construction of a new start signal (ATG) at the beginning of the large subunit, there is used the technique of a primer-started DNA synthesis. The large subunit begins at position 868 of the sequenced gene with the amino acid sequence Ser, Asn, Met. By means of the phosphotriester method (see R. Crea, A. Kaszewski, T. Hiros, K. Itakura, Proc. Natl. Acad. Sci. USA, 75, 5765-5769/1978), there is synthesised a 25 primer with the base sequence:

Met Ser Asn Met Trp Val
5'GGAATTC ATG AGC AAT ATG TGG GTT3'.

Figure 7:
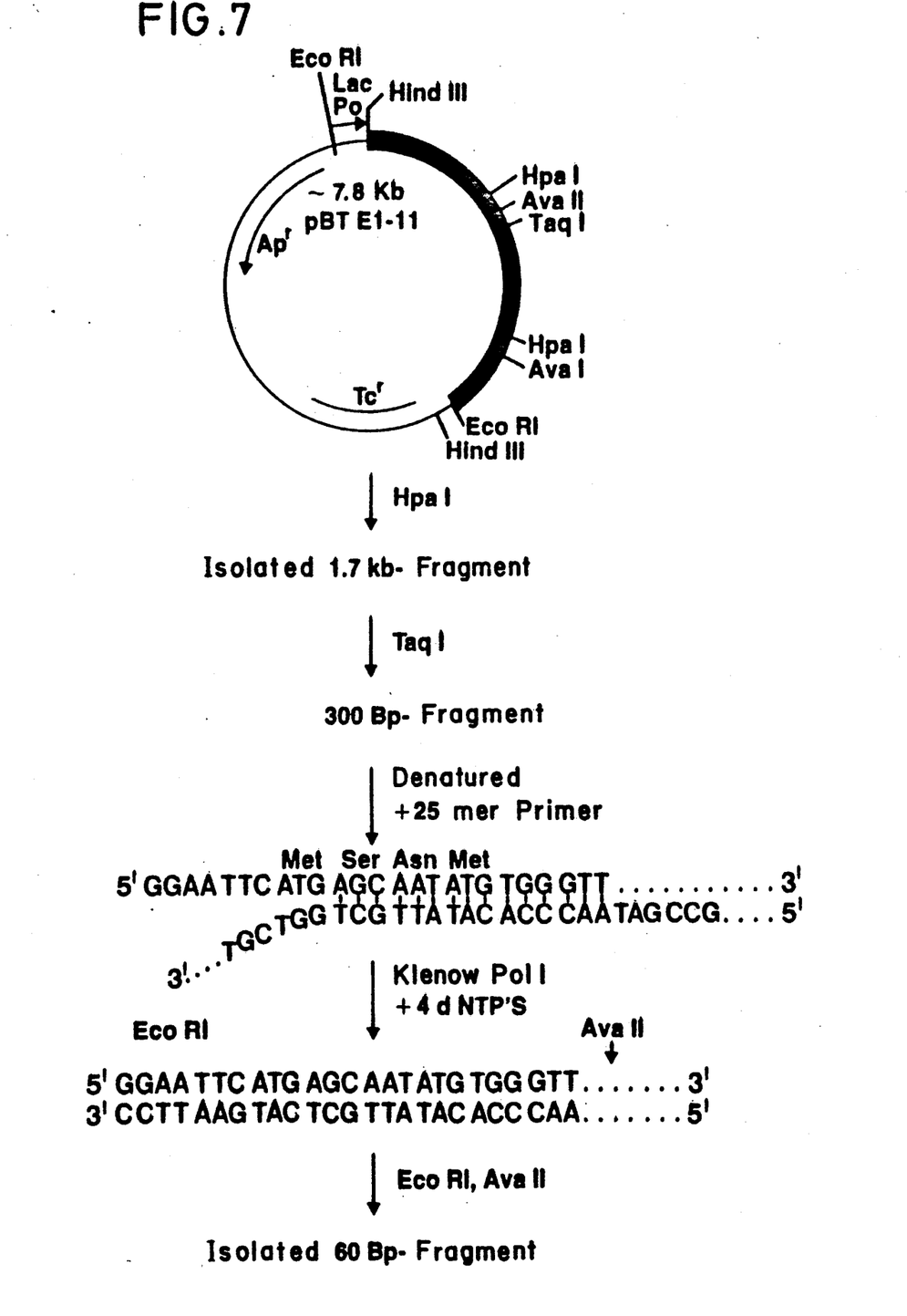
FIGS. 7 and 8 show the construction of the plasmid pBT 1000, DSM 3068P according to the present invention which codes the large subunit of penicillin G amidase and can bring about its expression.

This primer contains the recognition sequence for the restriction endonuclease Eco RI, an ATG start codon and the base sequence for the first 5 amino acids of the large subunit of the penicillin G amidohydrolase (FIG. 7).

From plasmid pBT E-1-11 is isolated, by splitting with Hpa I and after size separation in agarose gel, a 1.7 Kb fragment, this fragment is subsequently completely split with Taq I and a 0.30 Kb fragment isolated. About 0.5 μg. of this fragment are denatured by heating for 5 minutes at 100° C., 300 pmol of the untreated 25 primer are added to the batch and allowed to cool to ambient temperature. After the addition of 10 Units of DNA polymerase I (Klenow fragment) and all 4 desoxyribonucleotide triphosphates, incubation is carried out for 3 hours at ambient temperature and subsequently completely split with Ava II and Eco RI. After size separation in a 2.5% low melting agarose gel, the region in which a fragment with a size of 60 Bp would be banded is cut out, phenolysed, the sample extracted with diethyl ether and the DNA precipitated with ethanol.

Plasmid pKK 177-3 is completely split with Hind III and Eco RI. By means of size fractionation in a 0.8% agarose gel, there is isolated a 2.9 Kb-sized Hind III-Eco RI fragment.

Figure 8:
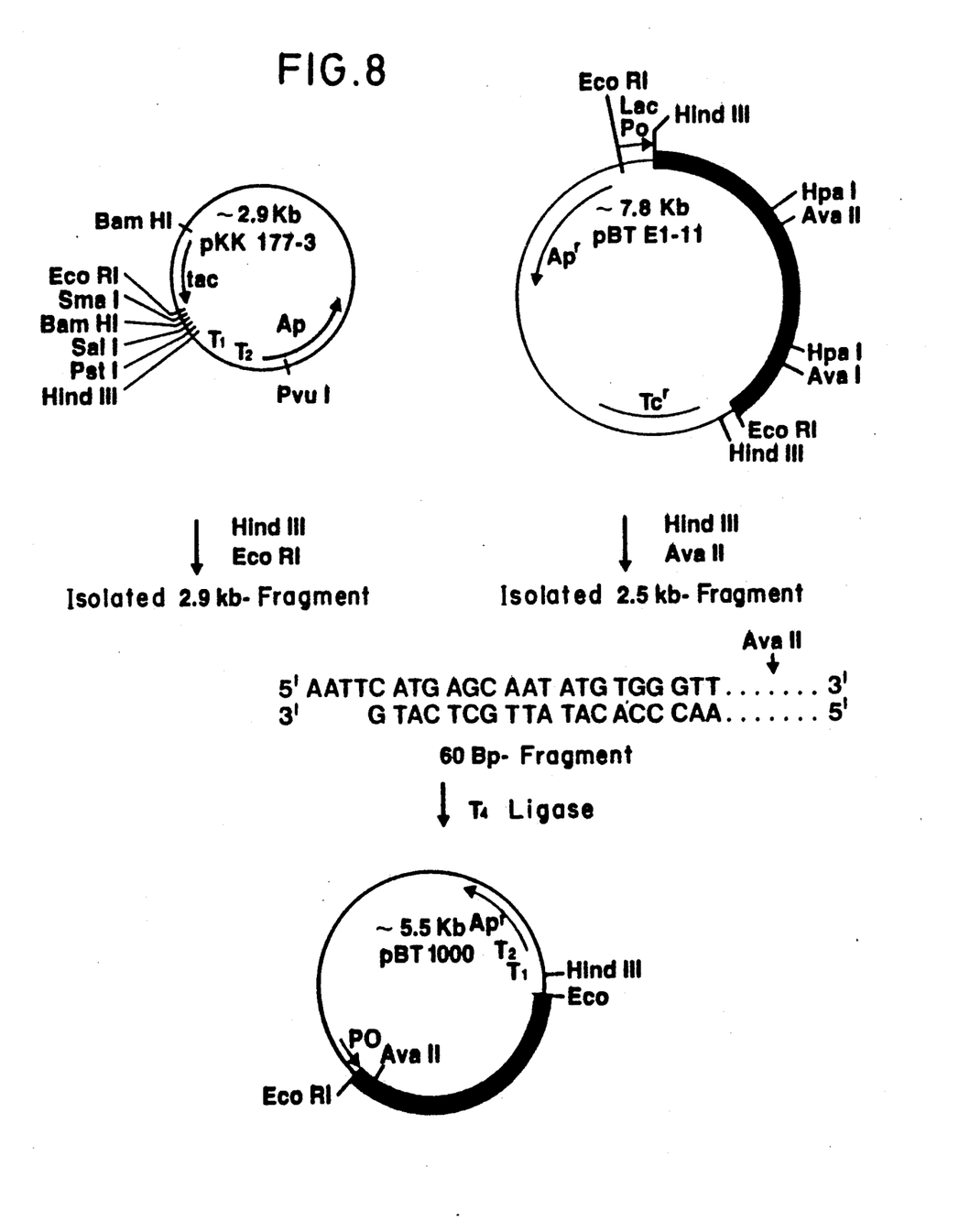

Plasmid pBT E1-11 is completely split with Hind III and Ava II. By means of size fractionation in a 0.8% agarose gel, there is isolated a 2.5 Kb Hind III-Ava II fragment (FIG. 8).

0.1 μg. each of these fragments are added to the ethanol-precipitated 60 Bp-Eco RI-Ava II fragment. After ligating overnight, the *Escherichia coli* strain 54-2 is transformed, the colonies are stamped on to Schleicher & Schüll BA 85 nitrocellulose filter paper and this filter transferred to LB agar plates which contain 20 μg./ml. amplicillin. After growing for 6 hours, the filters are transferred to LB agar plates which contain 20 μg./ml. amplicillin and 12.5 μg./ml. chloramphenicol and left to grow overnight. The DNA of the colonies is denatured and fixed on to nitrocellulose filter papers and subsequently hybridised with the radioactively-labelled 25 primer (with alterations according to R. W. Davis, D. Botstein and J. R. Roth (1980) in Advanced Bacterial Genetics, Cold Spring Harbor Laboratry). $10^6$ cpm per filter are used for the hybridisation. After washing at ambient temperature and at 42° C., the dried filters are exposed for 3 hours at ambient temperature with a Fuji EX X-ray film. 15 clones with positive signal are identified, the newly constructed restriction points are tested via Eco RI splitting and the expected DNA sequence confirmed by sequencing. The resulting plasmid is given the designation pBT 1000, DSM 3068P (FIG. 8). It codes the large subunit ($\beta$). It is detected by SDS gel chromatography (64 kD) and by immunological identification. Coloration with Coomassie blue showed that the $\beta$-subunit accounted for about 30 to 40% of the total protein.

EXAMPLE 4

Expression of the alpha-subunit of Penicillin G amidohydrolase

The *Escherichia coli* strain K12 54-2, which contains the plasmid pBT 702, is cultured for 12 hours at 30° C. in LB medium and subsequently diluted 1:2 in medium which contains 2 mM IPTG. After 4 hours, the cells are collected, digested with ultrasonics and the formation of the alpha-subunit demonstrated chromatographically on SDS gel and immunologically.

This result shows that the penicillin G amidase alpha-subunit is coded by the incomplete gene contained in the pBT 702.

EXAMPLE 5

The plasmids obtained according to Examples 1 and 3 are cloned into the compatible plasmids pACYC 184 and pBR 322 and transformed together into the host cell *Escherichia coli* K 12 54-2. Benzylpenicillin-splitting activity can be detected after de- and renaturing of the cell extracts.

In the above Examples and in the accompanying drawings, the given fragment sizes represent approximate statements obtained by comparison with size markers in agarose gels. The precise nucleotide number in the fragments can be determined on the basis of the given DNA sequence and the restriction splitting points recognisable therewith.

It is claimed:

1. Plasmid expressing penicillin G amidase in *E. coli* comprising a fraction of a penicillin G amidase gene, said fraction consisting of bases 79 to 705 and either bases 868 to 2538 or bases 868 to 2541 of the translation region counting from the 5' end of the complete gene as shown in FIG. 1, a promotor, a start codon, an operator and a ribosomal binding site all positioned in a reading frame which permits transcription of said fraction of a penicillin G amidase gene.

2. Plasmid according to claim 1, wherein said fraction is in the form of two separate fragments, said first fragment beginning with base 79, and said second fragment beginning with base 868, of the translation region counting from the 5' end of the complete gene as shown in FIG. 1.

3. Plasmid expressing a subunit of penicillin G amidase in *E. coli* comprising a fraction of a penicillin G amidase gene, said fraction consisting of bases 79 to 705 of the translation region of the penicillin G amidase gene counting from the 5' end of the complete gene as shown in FIG. 1, a promotor, a start codon, an operator, and a ribosomal binding site all positioned in a reading frame which permits transcription of said fraction of a penicillin G amidase gene.

4. Plasmid expressing a subunit of penicillin G amidase in *E. coli* comprising a fraction of a penicillin G amidase gene, said fraction consisting of either bases 868 to 2538 or bases 868 to 2541 of the translation region of the penicillin amidase gene counting from the 5' end of the complete gene as shown in FIG. 1, a promotor, a start codon, an operator and a ribosomal biding site all positioned in a reading frame which permits transcription of said fraction of a penicillin G amidase gene.

5. Plasmid according to claim 1, 2 or 3, wherein the base sequence ATG is connected with the 5' end of said fraction of said penicillin G amidase gene.

6. Plasmid according to claim 1, 2 or 3 further comprising a gene which confers resistance against an antibiotic.

7. Plasmid of claim 6, wherein said antibiotic is chloramphenicol.

8. Plasmid of claim 6, wherein said antibiotic is tetracycline.

9. Plasmid of claim 6, wherein said antibiotic is kanamycin.

10. Plasmid according to claim 1, 2 or 3 wherein it contains a tac promotor immediately before the beginning of the gene fraction.

11. Plasmid of claim 1, 2 or 3, wherein it contains a lac promotor immediately before the beginning of the gene fraction.

12. Plasmid pBT 702 (DSM 3067P).

13. Plasmid pBT 1000 (DSM 3068P).

14. Plasmid pBT 212 (DSM 3058P).

15. *E. coli* containing at least one plasmid of claim 1, 2 or 3.

16. *E. coli* of claim 1, comprising at least one of plasmids pBT 1000, pBT 702, and pBT 212.

17. Method for obtaining penicillin G amidase comprising subjecting *E. coli* transformed by at least one plasmid containing a first fraction of a gene for penicillin G amidase which contains bases 79 through 705 and a second fraction of a gene for penicillin G amidase which contains either bases 868 through 2538 or bases 868 through 2541 counting from the 5' end of the translation region of the complete gene as shown in FIG. 1 for both fractions, each of said plasmids containing a promotor, a start codon, an operator and a ribosomal binding site all positioned in a reading frame which permits transcription of said fraction of a pencillin G amidase gene, to conditions favoring expression of said gene fractions and collecting penicillin G amidase produced thereby, wherein said *E. coli* strain is capable of expressing said first and said second fraction of the penicillin G amidase gene.

18. Method according to claim 17, wherein said *E. coli* is transformed by one plasmid which comprises a first fragment beginning with base 79 and ending with base 705, and a separate second fragment beginning with base 868 and ending with either base 2538 or base 2541.

19. Method of claim 17, wherein said *E. coli* is selected from the group consisting of strains 54-2 (DSM 3066), DS 410 (DSM 3065), and DSM 3058.

20. Method for obtaining penicillin G amidase comprising subjecting a first *E. coli* transformed by a first plasmid containing a first fraction of a gene for penicillin G amidase, said fraction consisting of bases 79 to 705 of the translation region of the penicillin G amidase gene counting from the 5' end of the complete gene as shown in FIG. 1, a promotor, a start codon, an operator, and a ribosomal binding site all positioned in a reading frame which permits transcription of said fractions of a penicillin amidase gene, and a second *E. coli* transformed by a second fraction of a gene for penicillin G amidase, said fraction consisting of bases 868 to base 2538 or 2541 of the translation region of the penicillin G amidase gene counting from the 5' end of the complete gene as shown in FIG. 1, a promotor, a start codon, an operator, and a ribosomal binding site all positioned in a reading frame which permits transcription of said fraction of a penicillin amidase gene to conditions favoring expression of said gene fractions, mixing products of said expression to yield penicillin G amidase, and recovering said penicillin G amidase, wherein said first and second *E. coli* are each capable of expressing the fraction of the penicillin G amidase gene on the transforming plasmids.

21. Method for obtaining penicillin G amidase comprising subjecting *E. coli* transformed by a first plasmid containing a fraction of a gene for penicillin G amidase which consists of bases 79 to 705 of the translation region of the penicillin G amidase gene counting from the 5' end of the complete gene as shown in FIG. 1, a promotor, a start codon, an operator, and a ribosomal binding site all positioned in a reading frame which permits transcription of said fraction of a penicillin amidase gene and a second plasmid containing a second fraction of a gene for penicillin G amidase which consists of bases 868 to base 2538 or 2541 of the translation region of the penicillin G amidase gene counting from the 5' end of the complete gene as shown in FIG. 1, a promotor, a start codon, an operator, and a ribosomal binding site all positioned in a reading frame which permits transcription of said fraction of a penicillin amidase gene to conditions favoring expression of said gene fractions, and recovering penicillin G amidase produced thereby, wherein said *E. coli* is capable of expressing both fractions of the penicillin G amidase gene on the transforming plasmids.

22. *E. coli* of claim 15 comprising at least one of the plasmids pBT 1000, pBT 702, and pBT 212.

23. Penicillin G amidase produced by the method of claim 17.

* * * * *